US007662979B2

(12) United States Patent
Galante

(10) Patent No.: US 7,662,979 B2
(45) Date of Patent: Feb. 16, 2010

(54) OXINDOLEDIOXANS, SYNTHESIS THEREOF, AND INTERMEDIATES THERETO

(75) Inventor: Rocco J. Galante, Oakland, NJ (US)

(73) Assignee: Wyeth, Madison, NJ (US)

(*) Notice: Subject to any disclaimer, the term of this patent is extended or adjusted under 35 U.S.C. 154(b) by 305 days.

(21) Appl. No.: 11/807,257

(22) Filed: May 25, 2007

(65) Prior Publication Data
US 2007/0293686 A1 Dec. 20, 2007

Related U.S. Application Data

(60) Provisional application No. 60/808,394, filed on May 25, 2006.

(51) Int. Cl.
C07D 319/16 (2006.01)
(52) U.S. Cl. ............ 549/366; 549/200; 549/356; 549/358; 549/362; 548/427; 548/429; 548/430; 548/431
(58) Field of Classification Search .......... 549/200, 549/356, 357, 362, 366; 548/427, 429, 430, 548/431
See application file for complete search history.

(56) References Cited

U.S. PATENT DOCUMENTS

| 4,314,944 | A |   | 2/1982 | Huffman et al. |
|---|---|---|---|---|
| 5,126,366 | A |   | 6/1992 | Stack et al. |
| 5,166,367 | A |   | 11/1992 | Stack et al. |
| 5,189,171 | A |   | 2/1993 | Stack et al. |
| 5,235,055 | A |   | 8/1993 | Stack et al. |
| 5,245,051 | A |   | 9/1993 | Stack et al. |
| 5,318,988 | A |   | 6/1994 | Schohe-Loop et al. |
| 5,371,094 | A |   | 12/1994 | Heine et al. |
| 5,750,556 | A |   | 5/1998 | Mewshaw et al. |
| 5,756,532 | A |   | 5/1998 | Stack et al. |
| 5,869,490 | A |   | 2/1999 | Stack et al. |
| 5,914,263 | A | * | 6/1999 | Buizer et al. ............ 435/280 |
| 5,962,465 | A |   | 10/1999 | Stack et al. |
| 6,700,001 | B2 |   | 3/2004 | Gross et al. |
| 6,716,998 | B2 |   | 4/2004 | Gross et al. |
| 7,135,479 | B2 | * | 11/2006 | Zhou et al. ............ 514/291 |

FOREIGN PATENT DOCUMENTS

| DE | 4135474 A1 | 4/1993 |
|---|---|---|
| EP | 0771800 A3 | 1/1998 |
| EP | 0771801 B1 | 3/1999 |
| EP | 0939135 A1 | 9/1999 |
| EP | 0707007 B1 | 12/2001 |
| EP | 1375503 A1 | 1/2004 |
| WO | WO 0771800 A1 | 9/1991 |

OTHER PUBLICATIONS

Michael D. Ennis, et al., J. Med. Chem., 35, 3058-3066, (1992).
Joule et al., Heterocyclic Chemistry, 3d Ed. (1995 Stanley Thorne Ltd, Uk), 327-328, (1995).
Lilian Radesca et al., J. Med. Chem., 34, 3058-3065, (1991).
Panico et al., A Guide to IUPAC Nomenclature of Organic Compound (Recommendations) (1993).
I.L. Finar, Organic Chemistry, Vol. I, 721-722, (1959).
Beckett et al., Tetrahedron, 24, 6093-6109, (1968).
Heinrich et al., European Journal of Pharmacology, 552, 36-45, (2006).
Lahti et al., Molecular Pharmacology, 42, 432-438, (1992).
Tammingra et al., Archives of General Psychiatry, 43(4), 398-402, (1986).
Tammingra et al., Science, 200, 567-568, (1978).
M Makosza et al., J. Org. Chem., 48, 3860-3861, (1983).
M. Makosza et al., Synthesis, 1409-1410, (1994).
M. Makosza et al., Tetrahedron, 51(26), 7277-7286, (1995).
Galante et al., The 236$^{th}$ ACS Natl. Meeting, Phila, Pa, Aug. 17-21, 2008.
Mills et al., J. Chem. Soc., 2510-2524, (1930).
Corsini et al., Advances in Biochemical Psychopharmacology, 16, 645-648, (1977).
International Search Report, PCT/US2007/012622, mailed on Oct. 26, 2007.

* cited by examiner

Primary Examiner—Golam M M Shameem
(74) Attorney, Agent, or Firm—Choate Hall & Stewart LLP; Andrea L. C. Robidoux

(57) ABSTRACT

The present invention provides methods for preparing compounds having activity as dopamine autoreceptor agonists and partial agonists at the postsynaptic dopamine $D_2$ receptor. These compounds are useful for treating dopaminergic disorders, such as schizophrenia, schizoaffective disorder, Parkinson's disease, Tourette's syndrome, hyperprolactinemia, and drug addiction.

20 Claims, No Drawings

OXINDOLEDIOXANS, SYNTHESIS THEREOF, AND INTERMEDIATES THERETO

CROSS-REFERENCE TO RELATED APPLICATIONS

This application claims priority to U.S. provisional patent application Ser. No. 60/808,394, filed May 25, 2006, the entirety of which is hereby incorporated herein by reference.

FIELD OF THE INVENTION

The present invention relates to methods for synthesizing compounds useful as dopamine autoreceptor agonists and partial agonists at the postsynaptic dopamine $D_2$ receptor, derivatives thereof, and to intermediates thereto.

BACKGROUND OF THE INVENTION

The clinical treatment of schizophrenia has long been defined by the dopamine hypothesis of schizophrenia, which holds that schizophrenia is a result of hyperactivity of dopaminergic neurotransmission, particularly in limbic brain structures such as nucleus accumbens (the mesolimbic dopamine system). Indeed, the positive symptoms of schizophrenia (hallucinations, delusions, thought disorder) are successfully treated with neuroleptics, which block dopamine receptors. However, such treatment is accompanied by the production of movement disorders or dyskinesias (extrapyramidal side effects), due to the blockade of nigrostriatal dopamine receptors. In addition, neuroleptics do not treat the negative symptoms of schizophrenia (social withdrawal, anhedonia, poverty of speech) which are related to a relative hypoactivity of neurotransmission in the mesocortical dopamine system and which respond to treatment by dopamine agonists.

Efforts to induce antipsychotic activity with dopamine autoreceptor agonists have been successful (Corsini et al., Adv. Biochem. Psychopharmacol. 16, 645-648, 1977; Tamminga et al., Psychiatry 398-402, 1986). A method for determining intrinsic activity at the dopamine D2 receptor was recently published [Lahti et al., Mol. Pharm. 42, 432-438, (1993)]. As reported, intrinsic activity is predicted using the ratio of the "low-affinity agonist" (LowAg) state of the receptor and the "high-affinity agonist" (HighAg) state of the receptor, i.e. LowAg/HighAg. These ratios correlate with agonist, partial agonist, and antagonist activities for a given compound, which activities characterize a compound's ability to elicit an antipsychotic effect.

Dopamine autoreceptor agonists produce a functional antagonism of dopaminergic neurotransmission by the reduction of neuronal firing and the inhibition of dopamine synthesis and release. Since dopamine autoreceptor agonists are partial agonists at postsynaptic dopamine receptors, they provide a residual level of stimulation sufficient to prevent the production of dyskinesias. Indeed, partial agonists are capable of functioning as either agonists or antagonists depending on the level of dopaminergic stimulation in a given tissue or brain region, and would therefore be expected to have efficacy versus both positive and negative symptoms of schizophrenia. Thus, novel dopamine partial agonists are of great interest for the treatment of schizophrenia and related disorders.

SUMMARY OF THE INVENTION

As described herein, the present invention provides methods for preparing compounds having activity as dopamine autoreceptor agonists and partial agonists at the postsynaptic dopamine $D_2$ receptor. These compounds are useful for treating dopaminergic disorders, such as schizophrenia, schizoaffective disorder, Parkinson's disease, Tourette's syndrome, hyperprolactinemia, and drug addiction. Such compounds include those of formula 1:

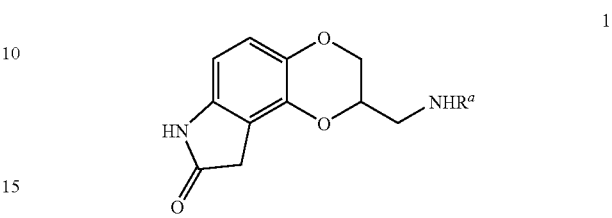

or a pharmaceutically acceptable salt thereof, wherein:
$R^a$ is —$(CH_2)_n$phenyl; and
n is 1 or 2.

The present invention also provides synthetic intermediates useful for preparing such compounds.

DETAILED DESCRIPTION OF CERTAIN EMBODIMENTS

The methods and intermediates of the present invention are useful for preparing compounds as described in, e.g. U.S. Pat. No. 5,756,532, in the name of Stack, et al, the entirety of which is incorporated herein by reference. The present synthesis is advantageous for preparing such compounds on a large scale using readily available reagents. In certain embodiments, the present compounds are generally prepared according to Scheme I set forth below:

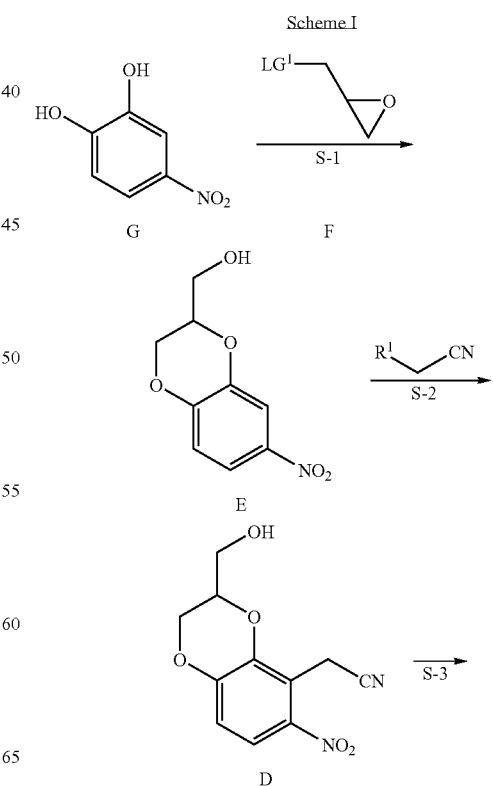

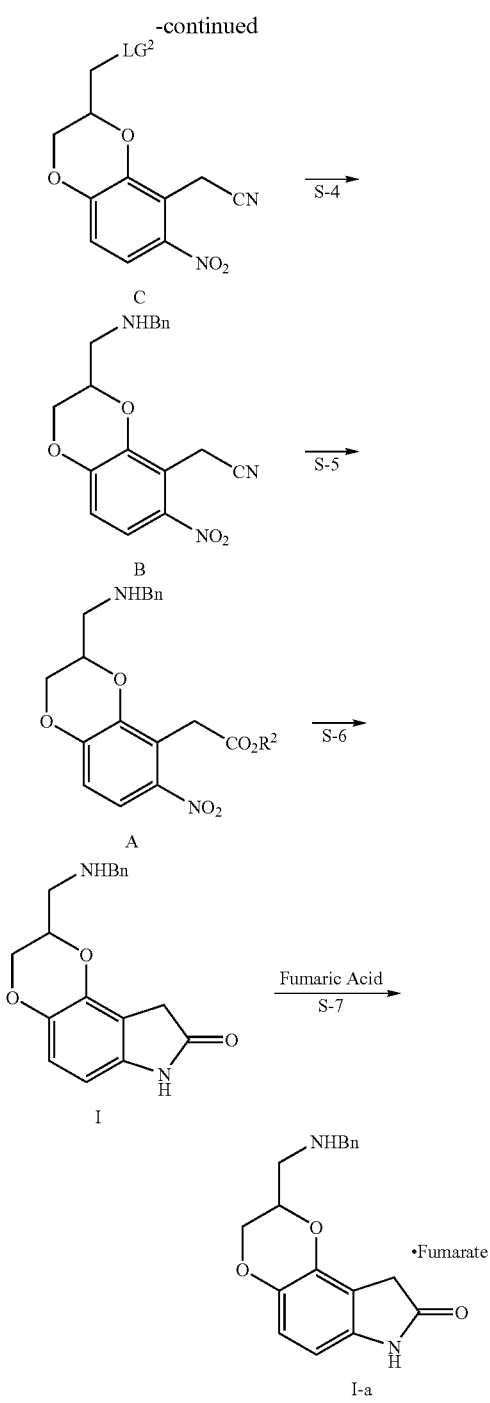

In Scheme I above, each of $R^1$, $R^2$, $LG^1$, and $LG^2$ is as defined below and in classes and subclasses as described herein.

At step S-1, the 4-nitro catechol G is treated with an epoxide of formula F, where $LG^1$ is a suitable leaving group, to form a compound of formula E. Suitable leaving groups are well known in the art, e.g., see, "Advanced Organic Chemistry," Jerry March, 5th Ed., pp. 445-448, John Wiley and Sons, N.Y. Such leaving groups include, but are not limited to, halogen, sulfonyloxy, optionally substituted alkylsulfonyloxy, optionally substituted alkenylsulfonyloxy, optionally substituted arylsulfonyloxy. Examples of suitable leaving groups include chloro, iodo, bromo, fluoro, methanesulfonyloxy (mesyloxy), tosyloxy, triflyloxy, nitrophenylsulfonyloxy (nosyloxy), and bromophenylsulfonyloxy (brosyloxy). In certain embodiments, $LG^1$ is halogen. In other embodiments, $LG^1$ is an optionally substituted alkylsulfonyloxy, optionally substituted alkenylsulfonyloxy, or optionally substituted arylsulfonyloxy group. In certain embodiments, $LG^1$ is halogen. In other embodiments, $LG^1$ is chloro.

The use of Makosza's vicarious nucleophilic substitution of hydrogen reaction in step S-2 is performed by treating a compound of formula E with the appropriately substituted acetonitrile compound to form a compound of formula D. As defined herein, the $R^1$ group is a suitable leaving group. In certain embodiments, $R^1$ is —OPhenyl, wherein the phenyl ring is substituted by one or more electron withdrawing groups. In other embodiments, $R^1$ is —OPhenyl, wherein the phenyl ring is substituted by chloro. According to another aspect, $R^1$ is chloro. The reaction at step S-2 is performed in the presence of a suitable base. In certain embodiments, the suitable base is a strong base. Such bases include metal alkoxides and metal hydrides. In certain embodiments, the base is potassium tert-butoxide. In certain embodiments, at least one equivalent of base is used at step S-2. In other embodiments, from about 2 to about 5 equivalents of base are used. In still other embodiments, from about 2.3 to about 4 equivalents of base are used.

At step S-3, the hydroxyl group of compound D is converted to a suitable leaving group, $LG^2$. The conversion of hydroxyl groups to leaving groups is well known to one of ordinary skill in the art an includes those methods described in March. Such $LG^2$ groups include, but are not limited to, halogen, alkoxy, sulphonyloxy, optionally substituted alkylsulphonyloxy, optionally substituted alkenylsulfonyloxy, and optionally substituted arylsulfonyloxy moieties. For the above mentioned "optionally substituted" moieties, the moieties may, for example, be optionally substituted with $C_{1-4}$ aliphatic, fluoro-substituted $C_{1-4}$ aliphatic, halogen, or nitro. Examples of suitable leaving groups include chloro, iodo, bromo, methanesulfonyloxy (mesyloxy), tosyloxy, triflyloxy, nitro-phenylsulfonyloxy (nosyloxy), and bromo-phenylsulfonyloxy (brosyloxy). According to one aspect of the present invention, $LG^2$ in compounds of formula D is toluenesulfonyloxy (tosyloxy). According to another aspect of the invention, a compound of formula E is allowed to react with toluenesulfonyl chloride (tosyl chloride) to afford a compound of formula D in which $LG^2$ is toluenesulfonyloxy (tosyloxy).

In certain embodiments step S-3 is performed in ethereal solvents, ester solvents, halogenated hydrocarbon solvents, or nitrile solvents. In certain embodiments this reaction is performed in tetrahydrofuran (THF), dichloromethane, acetonitrile, or isopropyl acetate. In other embodiments the reaction is run in THF. According to one aspect of the present invention, the reaction is run in the presence of suitable base. Exemplary bases include tertiary amines such as triethylamine (TEA), pyridine, and DIPEA. In certain embodiments, the reaction is run at a temperature that is between about −20° C. and about 40° C. In other embodiments, the reaction is conducted at a temperature of about 0° C.

At step S-4, the $LG^2$ group of formula D is displaced by benzylamine to form compound B. In certain embodiments, this displacement step is performed using from about 1 to about 5 equivalents of benzylamine. In other embodiments, this step is performed using from about 1 to about 3.5 equivalents of benzylamine. According to another aspect, S-4 is performed in a suitable medium.

A suitable medium is a solvent or a solvent mixture that, in combination with the combined compounds, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention include but are not limited to a protic solvent, a halogenated hydrocarbon, an ether, an ester, an aromatic hydrocarbon, a polar or a non-polar aprotic solvent, or any mixtures thereof. These and other such suitable solvents are well known in the art, e.g., see, "Advanced Organic Chemistry", Jerry March, 5$^{th}$ edition, John Wiley and Sons, N.Y. Such suitable solvents include polar aprotic solvents. In certain embodiments, step S-4 is performed in DMSO.

In certain embodiments, the displacement reaction at step S-4 is optionally performed in the presence of a suitable base. One of ordinary skill would recognize that the displacement of a leaving group by an amino moiety is achieved either with or without the presence of a suitable base. Such suitable bases are well known in the art and include organic and inorganic bases.

The conversion of the cyano group of formula B to the —CO$_2$R$^2$ group of formula A is achieved by hydrolysis at step S-5. In certain embodiments, step S-5 is performed in an alcoholic solvent such that a compound of formula A is formed wherein R$^2$ forms the corresponding ester. According to one aspect of the present invention, the hydrolysis at step S-5 is performed by treating a compound of formula B with gaseous HCl in an alcohol. In certain embodiments, the hydrolysis at step S-5 is performed by treating a compound of formula B with gaseous HCl in a lower alkyl alcohol. Such lower alkyl alcohols include methanol, ethanol, propanol, and isopropanol.

At step S-6, the nitro group of formula A is reduced to form the amine. The resulting compound cyclizes in situ to form a compound of formula I. One of ordinary skill in the art will recognize that there are many methods for reducing a nitro group to the corresponding amine. In certain embodiments, the reduction/cyclization step is performed by hydrogenation in the presence of a suitable catalyst. In other embodiments, the suitable catalyst is a platinum catalyst, Fe/HCl, or Sn/HCl. In still other embodiments, the suitable catalyst is platinum oxide.

At step S-7, the compound of formula I is optionally treated with fumaric acid to form the compound of formula I-a.

In certain embodiments, the present invention provides a method for preparing a compound of formula D:

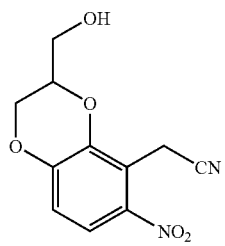

D comprising the steps of:
(a) providing a compound of formula E:

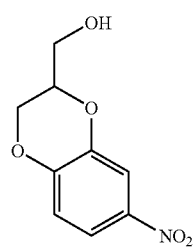

E and
(b) treating said compound of formula E with a compound of the formula

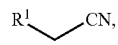

wherein R$^1$ is a suitable leaving group, in the presence of a suitable base.

As defined generally above, R$^1$ is a suitable leaving group. Leaving groups are well known in the art and include those described in detail in March. Exemplary leaving groups include halogen, alkoxy, and phenoxy groups wherein the phenyl ring is optionally substituted with one or more halogen, nitro, and ester groups. In certain embodiments, R$^1$ is a phenoxy group substituted with halogen.

As described above, step (b) is performed in the presence of a suitable base. In certain embodiments, the suitable base is a strong base. Exemplary strong bases include metal alkoxides and metal hydrides. In certain embodiments, step (b) is performed in the presence of a metal alkoxide. In other embodiments, step (b) is performed in the presence of potassium tert-butoxide.

In other embodiments, the present invention provides a method for preparing a compound of formula C:

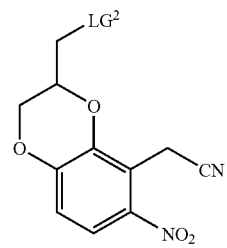

C wherein LG$^2$ is a suitable leaving group, comprising the steps of:
(a) providing a compound of formula D:

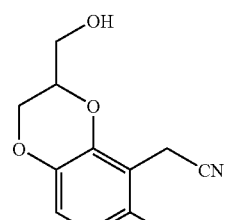

D and
(b) converting the free hydroxyl moiety of said compound of formula D into a suitable leaving group to afford a compound of formula C.

In step (b), the hydroxyl group of compound D is activated such that it becomes leaving group LG$^2$ that is subject to nucleophilic displacement. A suitable "leaving group" that is "subject to nucleophilic displacement" is a chemical group that is readily displaced by a desired incoming nucleophilic chemical entity. According to one aspect of the present invention, a compound of formula D is allowed to react with toluenesulfonyl chloride (tosyl chloride) to afford a compound of formula C in which LG$^2$ is toluenesulfonyloxy (tosyloxy).

In certain embodiments this reaction is performed in a suitable medium. In certain embodiments, the suitable medium is a polar aprotic solvent or halogenated hydrocarbon solvent such as tetrahydrofuran (THF), dichloromethane, acetonitrile, or isopropyl acetate. In other embodiments the suitable medium is dichloromethane.

According to one aspect of the present invention, the reaction is run in the presence of a suitable base. In certain embodiments, the suitable base is triethylamine (TEA). In other embodiments, the conversion of a compound D to a compound C is achieved in the presence of a catalytic amount of 4-(dimethylamino)pyridine.

Another aspect of the present invention provides a method for preparing a compound of formula B:

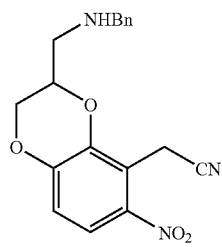

comprising the steps of:
(a) providing a compound of formula C:

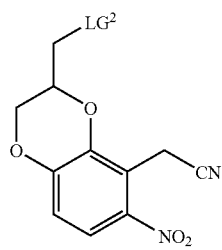

wherein LG$^2$ is a suitable leaving group;
and
(b) treating said compound of formula C with benzylamine.

In certain embodiments, the displacement step (b) is performed using from about 1 to about 5 equivalents of benzylamine. In other embodiments, this step is performed using from about 1 to about 3.5 equivalents of benzylamine. According to another aspect, step (b) is performed in a suitable medium.

A suitable medium is a solvent or a solvent mixture that, in combination with the combined compounds, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention are a protic solvent, a halogenated hydrocarbon, an ether, an ester, an aromatic hydrocarbon, a polar or a non-polar aprotic solvent, or any mixtures thereof. Such mixtures include, for example, mixtures of protic and non-protic solvents such as benzene/methanol/water; benzene/water; DME/water, and the like. In other embodiments, such suitable solvents include polar aprotic solvents. In certain embodiments, step (b) is performed in DMSO.

These and other such suitable solvents are well known in the art, e.g., see, "Advanced Organic Chemistry", Jerry March, 5$^{th}$ edition, John Wiley and Sons, N.Y.

In certain embodiments, the displacement reaction at step (b) is optionally performed in the presence of a suitable base. One of ordinary skill would recognize that the displacement of a leaving group by an amino moiety is achieved either with or without the presence of a suitable base. Such suitable bases are well known in the art and include organic and inorganic bases.

In certain embodiments, the present invention provides a method for preparing a compound of formula A:

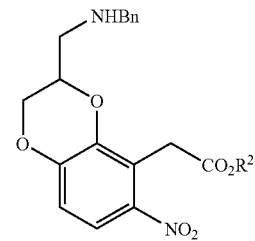

wherein R$^2$ is a carboxylate protecting group, comprising the steps of:
(a) providing a compound B:

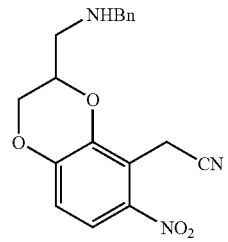

and
(b) hydrolyzing the nitrile moiety of said compound B to form a compound of formula A.

As defined above, R$^2$ is a suitable carboxylate protecting group. Protected carboxylic acids are well known in the art and include those described in detail in Greene (1999). Suitable protected carboxylic acids further include, but are not limited to, optionally substituted C$_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters. In certain embodiments, R$^2$ is an optionally substituted C$_{1-6}$ aliphatic ester or an optionally substituted aryl ester. In other embodiments, R$^2$ is a C$_{1-6}$ aliphatic ester. Such C$_{1-6}$ aliphatic esters include methyl, ethyl, propyl, and isopropyl.

The conversion of the cyano group of formula B to the —CO$_2$R$^2$ group of formula A is achieved by hydrolysis at step (b). In certain embodiments, step (b) is performed in an alcoholic solvent such that a compound of formula A is formed wherein $R^2$ forms the corresponding ester. According to one aspect of the present invention, the hydrolysis at step (b) is performed by treating a compound of formula B with gaseous HCl in an alcohol. In certain embodiments, the hydrolysis at step (b) is performed by treating a compound of formula B with gaseous HCl in a lower alkyl alcohol. Such lower alkyl alcohols include methanol, ethanol, propanol, and isopropanol.

In one aspect, the present invention provides methods for preparing chiral compounds of formula I-a according to the steps depicted in Scheme I, above. It will be appreciated that although Scheme I depicts a method for preparing a racemic compound of formula I-a, a desired enantiomer is similarly prepared using the appropriate chiral glycidyl ether of formula F. A general method for preparing a chiral compound of formula I-a is depicted in Scheme II, below.

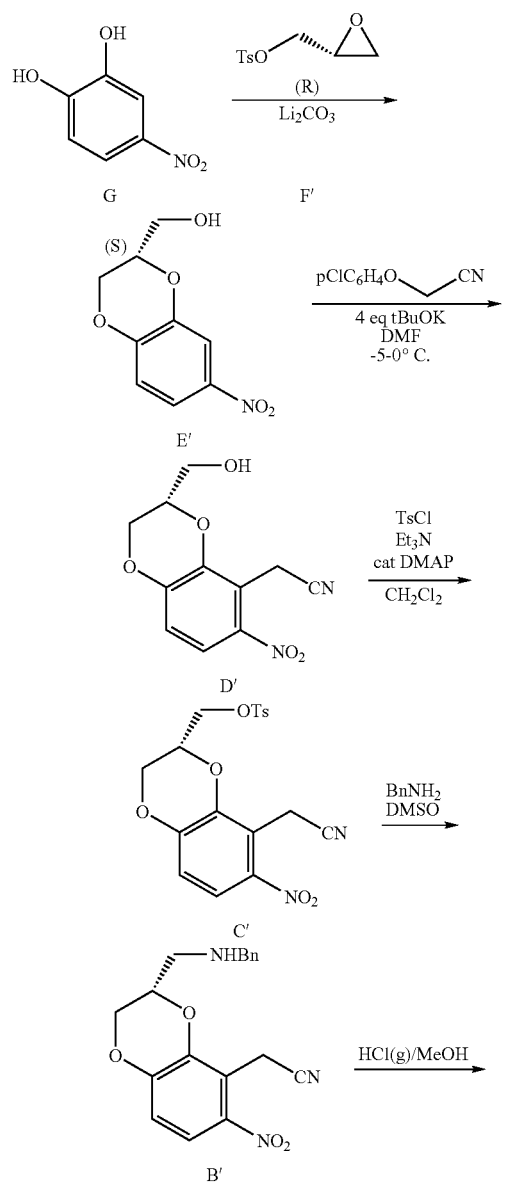

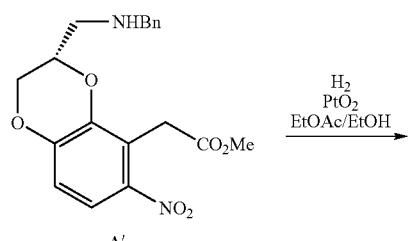

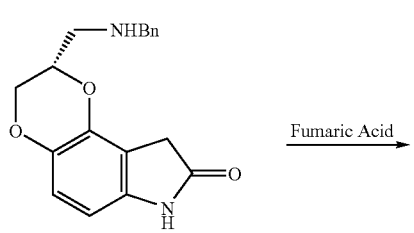

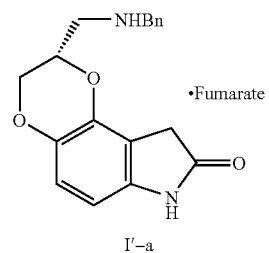

An alternate method for preparing a compound of formula E' is depicted in Scheme III below.

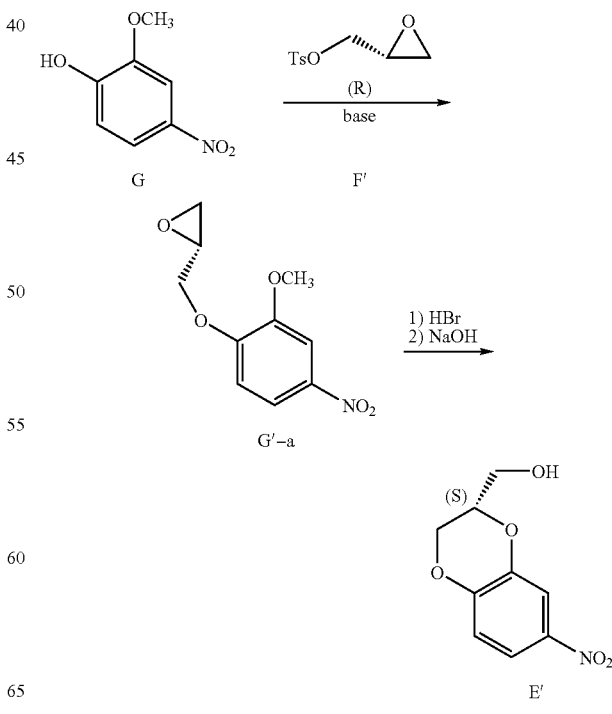

EXAMPLES

Melting points were obtained on a Buchi B-545 melting point apparatus and are uncorrected. $^1$H NMR spectra were obtained on a Bruker DPX 301 at 300 MHz and $^{13}$C NMR spectra were obtained on a Bruker DPX 301 75 MHz. The chemical shifts are reported in ppm relative to TMS (internal standard).

Example 1

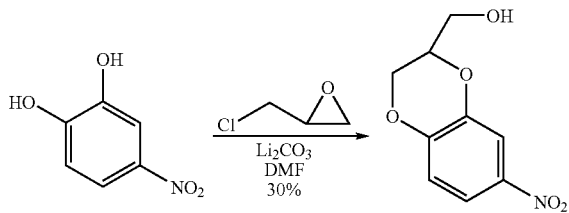

(7-nitro-2,3-dihydrobenzo[b][1,4]dioxin-2-yl)methanol: 4-Nitrocatechol (30 g, 0.19 mol), lithium carbonate (36 g, 0.49 mol), and epichlorohydrin (38 mL, 0.49 mol) in DMF (180 mL) were heated to 70-85° C. for 47 hours. Water was added and the mixture extracted with EtOAc (3×). Concentration of the combined EtOAc extracts and crystallization from MeOH gave the title compound, first crop, 5.98 g, 14.7% yield, mp 131.8-135° C. and second crop, 1.64 g, 4% yield, mp 133.1-136.7° C., (lit. mp 131-134° C.). $^1$H NMR (d6-DMSO) δ 7.78 (1H, dd, J=8.9, 2.7 Hz); 7.72 (1H, d, J=2.7 Hz); 7.11 (1H, d, J=8.9 Hz); 5.16 (1H, br s); 4.48 (1H, dd, J=11.4, 2.1 Hz); 4.32-4.23 (1H, m); 4.17 (1H, dd, J=11.4, 7.4 Hz); 3.66 (2H, br s).

Example 2

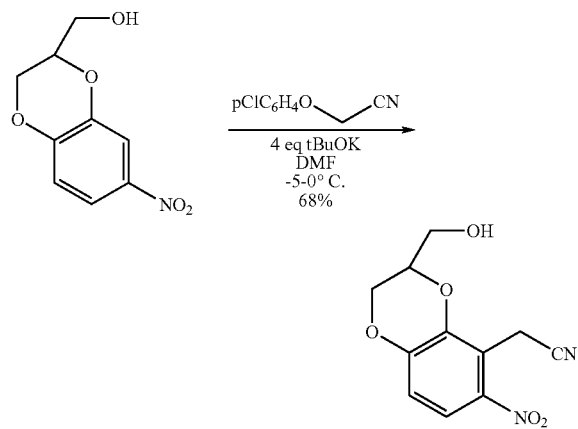

2-(3-(hydroxymethyl)-6-nitro-2,3-dihydrobenzo[b][1,4]dioxin-5-yl)acetonitrile: A solution of racemic (7-nitro-2,3-dihydrobenzo[b][1,4]dioxin-2-yl)methanol (1.00 g, 4.73 mmol) and 4-chlorophenoxyacetonitrile (827 mg, 4.94 mmol) in DMF (12 mL) was added dropwise to a solution of potassium tert-butoxide (2.12 g, 18.9 mmol) in DMF (20 mL) at −5-0° C. After the addition was complete (7 minutes), the reaction mixture was stirred for 1 hour at −5-0° C. The reaction mixture was acidified with 1 N HCl before drowning into water (200 mL). The mixture was extracted with EtOAc (3×100 mL) and the combined organic layers were washed with 1N NaOH (3×50 mL) to remove most of the 4-chlorophenol. After removal of solvent, the residue was purified by flash chromatography on silica gel, gradient elution using 2:3, 1:1, 3:2, 100:0 ethyl acetate/hexane, to give 139 mg, 14% recovered starting material and 804 mg, 68% yield of the title compound as a solid. $^1$H NMR (CDCl$_3$) δ 7.77 (1H, d, J=9.12 Hz); 7.01 (1H, d, J=9.12 Hz); 4.50-4.40 (2H, m); 4.30-3.91 (5H, m); 2.25-2.21 (1H, m). $^{13}$C NMR (CDCl$_3$) δ 148.07, 141.71, 141.55, 119.44, 117.07, 116.96, 115.71, 74.36, 65.31, 61.18, 14.89.

Example 3

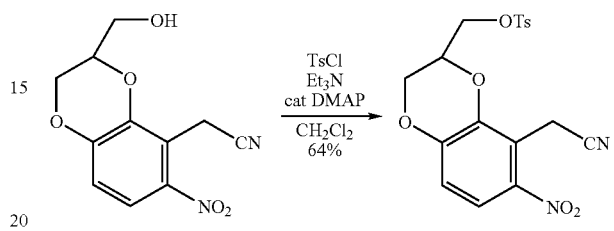

(8-(Cyanomethyl)-7-nitro-2,3-dihydrobenzo[b][1,4]dioxin-2-yl) methyl4-methylbenzene sulfonate: A solution of the 2-(3-(hydroxymethyl)-6-nitro-2,3-dihydrobenzo[b][1,4]dioxin-5-yl)acetonitrile formed at Example 2, (721.5 mg, 2.88 mmol), in CH$_2$Cl$_2$ (30 mL) was treated with tosyl chloride (604.7 mg, 3.17 mmol), triethylamine (602 µL, 4.32 mmol), and catalytic DMAP. After 4 hours, starting material was still present by TLC (100% CH$_2$Cl$_2$) and more tosyl chloride (60 mg) was added. After 18 hours the solution was washed with 10% aq HCl then 1N NaOH. Concentration and trituration with CH$_2$Cl$_2$ gave 746 mg, 64% yield of the title compound as a solid. $^1$H NMR (d6-DMSO) δ 7.82 (2H, d, J=8.31 Hz); 7.75 (1H, d, J=9.09 Hz); 7.48 (2H, d, J=8.13 Hz); 7.12 (1H, d, J=9.12 Hz); 4.74-4.66 (1H, m); 4.49-4.42 (2H, m); 4.30-4.15 (2H, m); 3.94 (2H, ab q, J$_{ab}$=16.83 Hz); 2.41 (3H, s).

Example 4

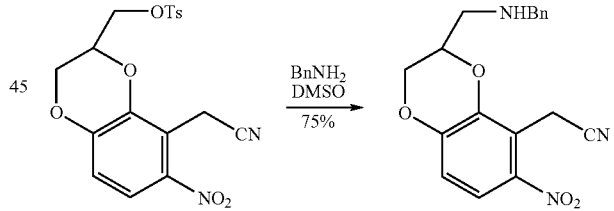

2-(3-((Benzylamino)methyl)-6-nitro-2,3-dihydrobenzo[b][1,4]dioxin-5-yl)acetonitrile: A solution of the tosylate compound formed at Example 3 (700 mg, 1.73 mmol) in DMSO (6 mL) was treated with benzyl amine (416 µL, 3.81 mmol). The solution immediately turned purple upon addition of benzyl amine. The mixture was heated to 85° C. for 23 hours and more benzyl amine (200 µL) was added. After another 18 hours at 85° C., the solution was cooled to room temperature, diluted with CH$_2$Cl$_2$, washed with 5% aq. NaHCO$_3$ (3×), and concentrated. Flash chromatography (eluting with CH$_2$Cl$_2$ then 40% EtOAc/CH$_2$Cl$_2$) gave 29.9 mg recovered starting material, 440 mg, 75% yield of the title compound. $^1$H NMR (CDCl$_3$) δ 7.75 (1H, d, J=9.15 Hz); 7.45-7.18 (5H, m); 6.97 (1H, d, J=9.12 Hz); 4.43-4.34 (2H, m); 4.21-4.01 (3H, m); 3.68 (2H, s); 3.05-2.93 (2H, m); 1.85 (1H, br s).

Example 5

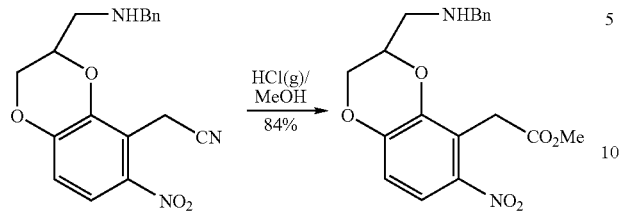

Methyl 2-(3-((benzylamino)methyl)-6-nitro-2,3-dihydrobenzo[b][1,4]dioxin-5-yl)acetate: Hydrogen chloride was bubbled through a solution of the nitrile from Example 4 (374 mg, 1.10 mmol) in MeOH (5 mL) at 0° C. for 1 hour. The flask was sealed and left in a freezer overnight. The mixture was concentrated, diluted with EtOAc, and washed with dilute aq. NaOH. The aqueous layer was extracted once with EtOAc and the combined organic layers concentrated to give 344 mg, 84% yield of the title compound as a dark oil. $^1$H NMR (CDCl$_3$) δ 7.67 (1H, d, J=9.09 Hz); 7.34-7.23 (5H, m); 6.92 (1H, d, J=9.09 Hz); 4.40-4.30 (2H, m); 4.17-4.11 (1H, m); 3.93-3.80 (4H, m); 3.67 (3H, s); 2.98-2.89 (2H, m).

Example 6

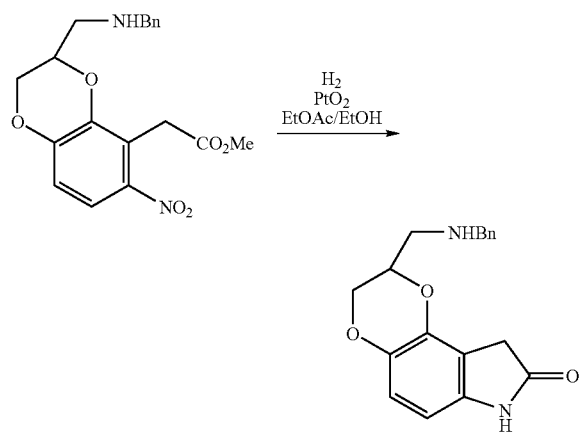

2-((Benzylamino)methyl)-2,3-dihydro-7H-[1,4]dioxino[2,3-e]indol-8(9H)-one: The methyl ester from Example 5 (43 mg) was dissolved in 1:1 ethyl acetate/ethanol (10 mL) and filtered through a syringe filter to remove insoluble material. Platinum oxide (35 weight percent) was added and the mixture placed under 50 psi of hydrogen gas on a Parr shaker overnight. TLC analysis with 95:5 CH$_2$Cl$_2$/MeOH showed consumption of starting material with a more polar product having been formed. The mixture was filtered through a 0.5 μm syringe filter, washing with 1:1 EtOAc/EtOH, and the filtrate concentrated under reduced pressure to a pale red-brown glass. The crude material was redissolved in ethanol (20 mL) and 20 μL of concentrated HCl were added. The solution was warmed to 70° C. and allowed to stir overnight. TLC of the reaction mixture (96:4 CH$_2$Cl$_2$/MeOH) showed the formation of a new product with no remaining starting material. The reaction mixture was cooled to ambient temperature and concentrated under reduced pressure to a light orange film. This was chromatographed over silica gel eluting with 96:4 CH$_2$Cl$_2$/MeOH. The title product was isolated in 22% yield.

I claim:

1. A method for preparing a compound of formula D:

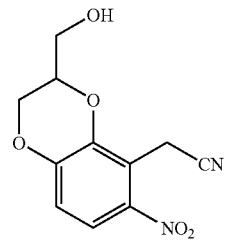

comprising the steps of:
(a) providing a compound of formula E:

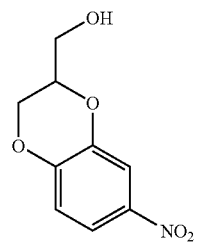

and
(b) treating said compound of formula E with a compound of the formula

wherein R$^1$ is a suitable leaving group, in the presence of a suitable base.

2. The method according to claim 1, wherein R$^1$ is halogen or a phenoxy group wherein the phenyl ring is optionally substituted one or more halogen, nitro, or ester groups.

3. The method according to claim 2, wherein R$^1$ is a phenyoxy group substituted with halogen.

4. The method according to claim 1, wherein the suitable base at step (b) is a strong base.

5. The method according to claim 4, wherein the strong base is a metal alkoxide or a metal hydride.

6. The method according to claim 5, wherein the strong base is potassium tert-butoxide.

7. The method according to claim 1, further comprising the step of converting the free hydroxyl moiety of said compound of formula D into a suitable leaving group to afford a compound of formula C:

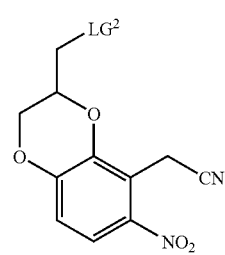

wherein LG$^2$ is a suitable leaving group.

8. The method according to claim 7, wherein LG² is tosyl.

9. The method according to claim 8, wherein the step of converting the free hydroxyl moiety of said compound of formula D into a suitable leaving group is performed in the presence of a suitable base.

10. The method according to claim 9, wherein the suitable base is triethylamine.

11. The method according to claim 7, further comprising the step of treating the compound of formula C with benzylamine to form a compound B:

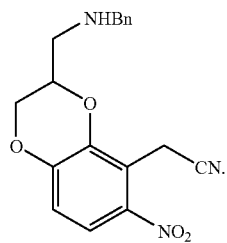

B

12. The method according to claim 11, wherein the compound of formula C is treated with about 1 to about 5 equivalents of benzylamine.

13. The method according to claim 11, further comprising the step of hydrolyzing the nitrile group of compound B to form a compound of formula A:

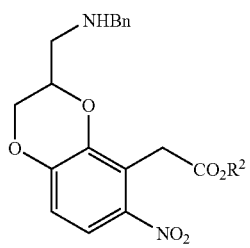

A wherein R² is a carboxylate protecting group.

14. The method according to claim 13, wherein R² is an optionally substituted $C_{1-6}$ aliphatic ester or an optionally substituted aryl ester.

15. The method according to claim 14, wherein R² is methyl, ethyl, propyl, or isoproyl.

16. The method according to claim 13, further comprising the step of reducing the nitro group of the compound of formula A to form compound I:

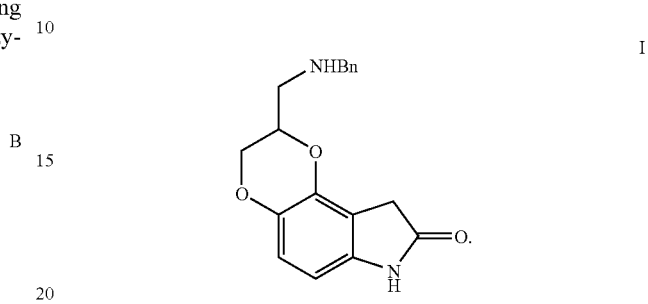

I

17. The method according to claim 16, wherein the reduction is performed by hydrogenation in the presence of a suitable catalyst.

18. The method according to claim 17, wherein the suitable catalyst is a platinum catalyst, Fe/HCl or Sn/HCl.

19. The method according to claim 18, wherein the suitable catalyst is platinum oxide.

20. The method according to claim 16, further comprising the step of treating the compound I with fumaric acid to form compound I-a:

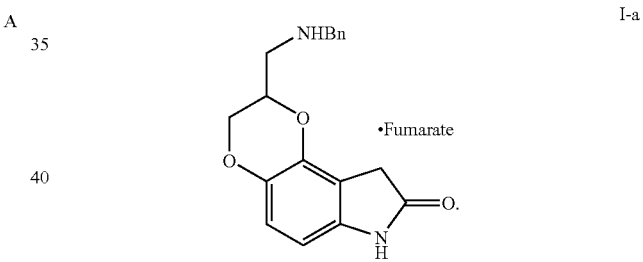

I-a

* * * * *